United States Patent [19]
Krenzer

[11] 3,984,228
[45] Oct. 5, 1976

[54] THIADIAZOLE SUBSTITUTED IMIDAZOLIDINES

[75] Inventor: John Krenzer, Oak Park, Ill.

[73] Assignee: Velsicol Chemical Corporation, Chicago, Ill.

[22] Filed: Sept. 11, 1975

[21] Appl. No.: 612,400

Related U.S. Application Data

[60] Division of Ser. No. 541,746, Jan. 17, 1975, Pat. No. 3,925,403, which is a continuation-in-part of Ser. No. 433,181, Jan. 14, 1974, abandoned, which is a continuation-in-part of Ser. No. 223,011, Feb. 2, 1972, abandoned.

[52] U.S. Cl. .................................................. 71/90
[51] Int. Cl.$^2$............................................ A01N 9/12
[58] Field of Search .......................................... 71/90

[56] References Cited
UNITED STATES PATENTS

| | | | |
|---|---|---|---|
| 3,651,075 | 3/1972 | Miller ...................................... | 71/90 |
| 3,657,264 | 4/1972 | Rucker et al. ........................... | 71/90 |
| 3,773,780 | 11/1973 | Metzger et al. ......................... | 71/90 |

*Primary Examiner*—Glennon H. Hollrah
*Attorney, Agent, or Firm*—Robert J. Schwarz; Dietmar H. Olesch

[57] ABSTRACT

This invention discloses new compounds of the formula

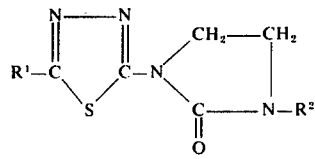

wherein $R^1$ is selected from the group consisting of isopropyl, t-butyl and trifluoromethyl; and $R^2$ is lower alkyl. Further disclosed are herbicidal compositions utilizing the above-described compounds.

2 Claims, No Drawings

THIADIAZOLE SUBSTITUTED IMIDAZOLIDINES

This application is a division of copending application Ser. No. 541,746, filed Jan. 17, 1975 now U.S. Pat. No. 3,925,403, which is a continuation in part of application Ser. No. 433,181, filed Jan. 14, 1974, now abandoned; which is a continuation in part of application Ser. No. 223,011, filed Feb. 2, 1972, now abandoned.

This invention relates to new compositions of matter and more specifically relates to new chemical compounds of the formula

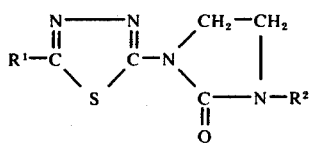

wherein $R^1$ is selected from the group consisting of isopropyl, t-butyl and trifluoromethyl; and $R^2$ is lower alkyl.

The compounds of the present invention are unexpectedly useful as herbicides.

The term lower as used herein designates a straight or branched carbon chain of up to about 6 carbon atoms.

The compounds of this invention can be readily prepared from a thiadiazole substituted urea of the formula

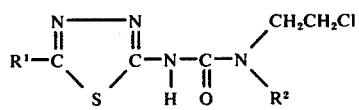

wherein $R^1$ and $R^2$ are as heretofore described by treatment with aqueous sodium or potassium hydroxide. This reaction can be effected by adding the aqueous sodium hydroxide having a concentration of from about 0.5 to about 50 percent by weight to the urea of Formula II at room temperature with stirring. The described product is formed as a solid and can be used as such or can be further purified by standard techniques such as recrystallization and the like.

The thiadiazole substituted ureas of Formula II can be prepared from a corresponding hydroxy substituted urea of the formula

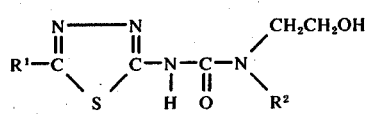

wherein $R^1$ and $R^2$ are heretofore described, by reaction with thionyl chloride. This reaction can be effected by refluxing the urea dissolved in a suitable solvent such as benzene in the presence of a slight excess molar amount of the thionyl chloride. Upon completion of the reaction the product is recovered by stripping off the solvent and unreacted thionyl chloride.

The ureas of Formula III can be prepared from a thiadiazol isocyanate dimer of the formula

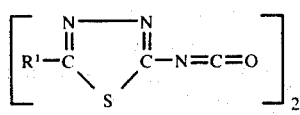

wherein $R^1$ is as heretofore described, by reaction with a beta-hydroxyethylamine of the formula

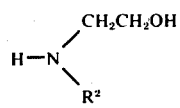

wherein $R^2$ is as heretofore described. This reaction can be conveniently effected by adding the amine of Formula V to a suspension of the isocyanate of Formula IV and thereafter refluxing the mixture for a period of from about 5 minutes to about 3 hours. Suitable solvents for the isocyanate are inert organic solvents such as benzene, toluene, ethyl acetate and the like. Upon completion of the reaction the product can be recovered by evaporating the solvent or can be left in solution for reaction with thionyl chloride as hereinabove described.

The isocyanate dimer of Formula V can be prepared from the corresponding amino compound of the formula

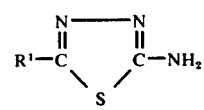

wherein $R^1$ is as heretofore described by reaction with phosgene. This reaction can be effected by adding a solution of the compound of Formula VI to a saturated solution of phosgene in a suitable solvent such as ethyl acetate. The resulting mixture can then be stirred for a period of from 1 to 18 hours to ensure completion of the reaction. After this time nitrogen gas can be passed through the reaction mixture to remove unreacted phosgene and thereafter the desired product can be recovered as a precipitate by filtration of the reaction mixture.

The preparation of the compounds of the present invention is more specifically illustrated in the following examples.

EXAMPLE 1

Preparation of 2-t-Butyl-1,3,4-thiadiazol-5-yl Isocyanate Dimer

A saturated solution of phosgene in ethyl acetate (100 ml) was charged into a glass reaction vessel equipped with a mechanical stirrer. A slurry of 2-t-butyl-5-amino-1,3,4-thiadiazole (10 grams) in ethyl acetate (300 ml) was added to the reaction vessel and the resulting mixture was stirred for a period of about 16 hours resulting in the formation of a precipitate. The reaction mixture was then purged with nitrogen gas to remove unreacted phosgene. The purged mixture was then filtered to recover the desired product 2-t-butyl-1,3,4-thiadiazol-5-yl isocyanate dimer as a solid having a melting point of 261° to 263°C.

EXAMPLE 2

Preparation of
N-(β-Hydroxyethyl)-N-methyl-N'-(2-t-butyl-1,3,4-thiadiazol-5-yl)urea 2-t-Butyl-1,3,4-thiadiazol-5-yl isocyanate dimer (10 grams), N-methyl-N-β-hydroxyethylamine (4.4 grams) and ethyl acetate (50 ml) were charged into a glass reaction vessel equipped with a mechanical stirrer, reflux condenser and thermometer. The reaction mixture was heated at reflux with stirring for a period of about 2 hours. After this time the reaction mixture was stripped of solvent under reduced pressure to yield the desired product N-(β-hydroxyethyl)-N-methyl-N'-(2-t-butyl-1,3,4-thiadiazol-5-yl)urea as an oily residue.

EXAMPLE 3

Preparation of
N-(β-Chloroethyl)-N-methyl-N'-(2-t-butyl-1,3,4-thiadiazol-5-yl)urea The N-(β-hydroxyethyl)-N-methyl-N'-(2-t-butyl-1,3,4-thiadiazol-5-yl)urea prepared in Example 2, thionyl chloride (5 ml) and benzene (100 ml) were charged into a glass reaction vessel equipped with a mechanical stirrer, thermometer and reflux condenser. The reaction mixture was heated at reflux, with stirring, for a period of about one hour. After this time the benzene and unreacted thionyl chloride were stripped from the reaction mixture under reduced pressure to yield the desired product N-(β-chloroethyl)-N-methyl-N'-(2-t-butyl-1,3,4-thiadiazol-5-yl)urea as the residue.

EXAMPLE 4

Preparation of
1-(2-t-Butyl-1,3,4-thiadiazol-5-yl)-3-methyl-1,3-imidazolidin-2-one The product N-(β-chloroethyl)-N-methyl-N'-(2-t-butyl-1,3,4-thiadiazol-5-yl)urea prepared in Example 3 was charged into a glass reaction flask equipped with a mechanical stirrer. A solution of potassium hydroxide (9 grams) dissolved in water (50 ml) was added to the flask with stirring. After the addition was completed stirring was continued for a period of about 1 hour resulting in the formation of a solid product. This product was recovered by filtration, was air dried and was recrystallized from cyclohexane to yield the desired product 1-(2-t-butyl-1,3,4-thiadiazol-5-yl)-3-methyl-1,3-imidazolidin-2-one having a melting point of 127° to 129°C.

EXAMPLE 5

Preparation of 2-Trifluoromethyl-1,3,4-thiadiazol-5-yl Isocyanate Dimer

A saturated solution of phosgene in ethyl acetate (100 ml) was charged into a glass reaction flask equipped with a mechanical stirrer. A slurry of 2-trifluoromethyl-5-amino-1,3,4-thiadiazole (10 grams) in ethyl acetate (300 ml) was added to the reaction vessel and the resulting mixture was stirred for a period of about 16 hours resulting in the formation of a precipitate. The reaction mixture was then purged with nitrogen gas to remove unreacted phosgene. The purged mixture was then filtered to recover the desired product 2-trifluoromethyl-1,3,4-thiadiazol-5-yl isocyanate dimer.

EXAMPLE 6

Preparation of
N-(β-Hydroxyethyl)-N-methyl-N'-(2-trifluoromethyl-1,3,4-thiadiazol-5-yl)urea 2-Trifluoromethyl-1,3,4-thiadiazol-5-yl isocyanate dimer (8 grams), N-methyl-N-β-hydroxyethylamine (3.1 grams) and benzene (40 ml) were charged into a glass reaction vessel equipped with a mechanical stirrer, reflux condenser and thermometer. The reaction mixture was heated at reflux, with stirring for a period of about 10 minutes. After this time the reaction mixture was stripped of solvent under reduced pressure to yield the desired product N-(β-hydroxyethyl)-N-methyl-N'-(2-trifluoromethyl-1,3,4-thiadiazol-5-yl)urea as an oily residue.

EXAMPLE 7

Preparation of
N-(β-Chloroethyl)-N-methyl-N'-(2trifluoromethyl-1,3,4-thiadiazol-5-yl)urea The N-(β-hydroxyethyl)-N-methyl-N'-(2-trifluoromethyl-1,3,4-thiadiazol-5-yl)urea prepared in Example 6, thionyl chloride (5 ml) and benzene (50 ml) were charged into a glass reaction vessel equipped with a mechanical stirrer, thermometer and reflux condenser. The reaction mixture was heated at reflux with stirring, for a period of about one-half hour. After this time the benzene and unreacted thionyl chloride were stripped from the reaction mixture under reduced pressure to yield the desired product N-(β-chloroethyl)-N-methyl-N'-(2-trifluoromethyl-1,3,4-thiaidazol-5-yl)urea as a solid residue.

EXAMPLE 8

Preparation of
1-(2-Trifluoromethyl-1,3,4-thiadiazol-5-yl)-3-methyl-1,3-imidazolidin-2-one The product N-(β-chloroethyl-N-methyl-N'-(2-trifluoromethyl-1,3,4-thiadiazol-5-yl)urea prepared in Example 7 was charged into a glass reaction vessel. A solution of potassium hydroxide (8 grams) dissolved in water (50 ml) was added to the flask with stirring. The resulting mixture was stirred for a period of about 1 hour. The resulting solid product was recovered by filtration, was dried and was recrystallized from methanol to yield the desired product 1-(2-trifluoromethyl-1,3,4-thiadiazol-5-yl)-3-methyl-1,3-imidazolidin-2-one having a melting point of 182° to 184°C.

Additional compounds within the scope of the present invention can be prepared by the procedures detailed in the foregoing examples. In the following examples are given the essential starting materials required for preparing the indicated named compounds.

EXAMPLE 9

2-Trifluoromethyl-5-amino-1,3,4-thiadiazole + phosgene + N-ethyl-N-β-hydroxyethylamine + thionyl chloride + potassium hydroxide = 1-(2-trifluoromethyl-1,3,4-thiadiazol-5-yl)-3-ethyl-1,3-imidazolidin-2-one; m.p. 99°–101°C.

EXAMPLE 10

2-t-Butyl-5-amino-1,3,4-thiadiazole + phosgene + N-propyl-N-β-hydroxyethylamine + thionyl chloride + sodium hydroxide = 1-(2-t-butyl-1,3,4-thiadiazol-5-yl)-3-propyl-1,3-imidazolidin-2-one.

EXAMPLE 11

2-Trifluoromethyl-5-amino-1,3,4-thiadiazole + phosgene + N-n-butyl-N-β-hydroxyethylamine + thionyl chloride + potassium hydroxide = 1-(2-trifluoromethyl-1,3,4-thiadiazol-5-yl)-3-n-butyl-1,3-imidazolidin-2-one.

EXAMPLE 12

2-Isopropyl-5-amino-1,3,4-thiadiazole + phosgene + N-methyl-N-β-hydroxyethylamine + thionyl chloride + sodium hydroxide = 1-(2-isopropyl-1,3,4-thiadiazol-5-yl)-3-methyl-1,3-imidazolidin-2-one.

EXAMPLE 13

2-Isopropyl-5-amino-1,3,4-thiadiazole + phosgene + N-n-hexyl-N-β-hydroxyethylamine + thionyl chloride + potassium hydroxide = 1-(2-isopropyl-1,3,4-thiadiazol-5-yl)-3-n-hexyl-1,3-imidazolidin-2-one.

EXAMPLE 14

2-t-Butyl-5-amino-1,3,4-thiadiazole + phosgene + N-ethyl-N-β-hydroxyethylamine + thionyl chloride + potassium hydroxide = 1-(2-t-butyl-1,3,4-thiadiazol-5-yl)-3-ethyl-1,3-imidazolidin-2-one.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 15

| Preparation of a Dust | |
| --- | --- |
| Product of Example 4 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like, carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atazine, trietazine, simetone, prometone, propazine, ametryne and the like; chloroacetamide herbicides such as 4-(chloroacetyl)morpholine, 1-(chloroacetyl)piperidine and the like; chlorinated aliphatic acid herbicides such as TCA, dalapon, 2,3-dichloropropionic acid, 2,2,3-TPA and the like, chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morningglory, bedstraw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle, or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, wintercress, horsenettle, nutsedge, milkweed and sicklepod.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively non-toxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of an active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after seeding the pots were sprayed with water until the soil was wet and the compound 1-(2-t-butyl-1,3,4-thiadiazol-5-yl)-3-methyl-1,3-imidazolidin-2-one formulated as an aqueous emulsion of an acetone solution containing emulsifiers was sprayed at a concentration of 8 pounds per acre on the surface of the soil.

After spraying, the soil containers were placed in the greenhouse and provided with supplementary heat as required and daily or more frequent watering. The plants were maintained under these conditions for a period of from 15 to 21 days, at which time the condition of the plants and the degree of injury to the plants was rated on a scale of from 0 to 10, as follows: 0 = no injury, 1,2 = slight injury, 3,4 = moderate injury, 5,6 = moderately severe injury, 7,8,9 = severe injury and 10 = death. The effectiveness of these compounds is demonstrated by the following data:

TABLE I

| Weed Species | Injury Rating |
| --- | --- |
| Barnyardgrass | 10 |
| Crabgrass | 10 |
| Downy Brome | 7 |
| Foxtail | 10 |
| Johnsongrass | 7 |
| Wild Oats | 9 |
| Coffeeweed | 10 |
| Curly Dock | 10 |
| Velvetleaf | 10 |
| Wild Mustard | 10 |

The herbicidal activity of the compounds of this invention was also demonstrated by experiments carried out for the post-emergence control of a variety of weeds. In these experiments 1-(2-t-butyl-1,3,4-thiadiazol-5-yl)-3-methyl-1,3-imidazolidin-2-one was formulated as an aqueous emulsion and sprayed at 8 pounds per acre on the foliage of the weeds that have attained a prescribed size. After spraying the plants were placed in a greenhouse and watered daily or more frequently. Water was not applied to the foliage of the treated plants. The severity of the injury was determined 10 to 15 days after treatment and was rated on the scale of from 0 to 10 hertofore described. The effectiveness of these compounds is demonstrated by the following data:

TABLE II

| Weed Species | Injury Rating |
|---|---|
| Barnyardgrass | 9 |
| Crabgrass | 10 |
| Downy Brome | 10 |
| Foxtail | 10 |
| Johnsongrass | 10 |
| Wild Oats | 10 |
| Coffeeweed | 10 |
| Curly Dock | 10 |
| Bindweed | 9 |
| Matricaria | 10 |
| Pigweed | 10 |
| Velvetleaf | 10 |
| Wild Mustard | 10 |

I claim:

1. A herbicidal composition comprising an inert carrier and, as an essential active ingredient, in a quantity toxic to weeds, a compound of the formula

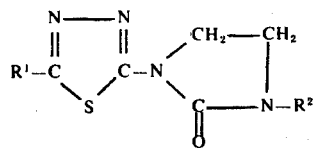

wherein $R^1$ is selected from the group consisting of isopropyl, t-butyl and trifluoromethyl; and $R^2$ is lower alkyl.

2. A method of controlling weeds which comprises contacting said weeds with an effective amount of a herbicidal composition of claim 1.

* * * * *